United States Patent [19]

Hartenstein et al.

[11] 4,228,179

[45] Oct. 14, 1980

[54] 3-OXO-2-AZASPIRO-2-(N-METHYL)-ACETA-MIDES

[75] Inventors: Johannes Hartenstein, Stegen-Wittental; Gerhard Satzinger, Denzlingen; Manfred Herrmann, St. Peter; Wolfgang Heldt, Emmendingen, all of Fed. Rep. of Germany

[73] Assignee: Warner-Lambert Company, Morris Plains, N.J.

[21] Appl. No.: 924,277

[22] Filed: Jul. 13, 1978

Related U.S. Application Data

[63] Continuation of Ser. No. 746,776, Dec. 2, 1976, abandoned.

[30] Foreign Application Priority Data

Dec. 19, 1975 [DE] Fed. Rep. of Germany ....... 2557220

[51] Int. Cl.² ..................... A61K 31/40; C07D 209/54
[52] U.S. Cl. ................. 424/274; 260/376.38; 260/326.43
[58] Field of Search ...................... 260/326.38, 326.43; 424/274

[56] References Cited

U.S. PATENT DOCUMENTS

2,935,515   5/1960   Larrabee ........................... 260/326.5

OTHER PUBLICATIONS

Burger, A. "Medicinal Chemistry," 2nd ed., Interscience Publishers Inc., N.Y., 1960, p. 491.

*Primary Examiner*—Donald G. Daus
*Assistant Examiner*—Lisa Jones
*Attorney, Agent, or Firm*—Albert H. Graddis

[57] ABSTRACT

The present invention is concerned with new N-substituted spirolactams and their preparation.

24 Claims, No Drawings

3-OXO-2-AZASPIRO-2-(N-METHYL)-ACETAMIDES

This is a continuation of Ser. No. 746,776, filed Dec. 2, 1976, now abandoned.

The new N-substituted spirolactams according to the present invention, which possess valuable pharmacodynamic properties, are compounds of the general formula:

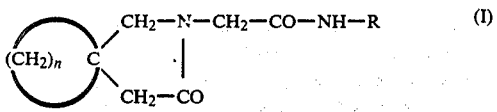

wherein R is a hydrogen atom or a saturated or unsaturated lower aliphatic radical and n is 4, 5 or 6.

The expression saturated or unsaturated lower aliphatic radical is, according to the present invention, a straight or branched chain alkyl radical containing up to 5 carbon atoms which can optionally contain a double or triple bond.

Alkyl radicals containing up to 3 carbon atoms are preferred, i.e. methyl, ethyl, n-propyl and isopropyl radicals, as well as unsaturated radicals containing 3 to 5 carbon atoms, especially allyl and propynyl radicals.

When n is 4, general formula (I) contains a cyclopentyl ring and the compound is a 3-oxo-2-azaspiro[4,4]nonane-2-acetamide. When n is 5, then the compound is a 3-oxo-2-azaspiro[4,5]-decane.

German Patent Specification No. 1,620,608 describes certain N-substituted monocyclic lactams which can be used in the treatment of travel sickness, hyperkinesias, hypertonias, epilepsy and the like.

Subsequent to the application for German Patent Specification No. 1,620,608, the mechanism of the compounds was described more precisely. As can be seen from Arch. int. Pharmacodyn., 166, 238–251/1967, the compound 2-oxo-1-pyrrolidine-acetamide (Piracetam; UCB 6215) is completely ineffective against cramp induced by pentetrazole and by semicarbazide.

We have now found that the new compounds of formula (I) have a remarkable protective action in the semicarbazide cramp animal model and in addition some of the new compounds show a considerable protective effect against pentetrazole cramp. Since the compounds of formula (I) have a relatively low toxicity, they possess properties which appear to be favorable in the treatment of certain cerebral and spinal diseases; for example, they are suitable for the therapy of certain forms of epilepsy, dizziness, hypokinesia and cerebral damage and they bring about an improvement of the cerebral functions. In addition, they are also effective geriatric drugs.

The new compounds of formula (I) can be prepared by one of the following methods:

(A) reaction of an alkali metal salt of a compound of the formula:

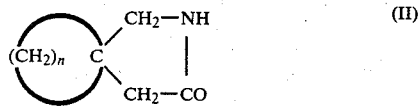

wherein n has the same meaning as above, with a haloacetamide of the formula:

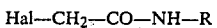

wherein R has the same meaning as above and Hal is an iodine, bromine or chlorine atom; or (B) reaction of a compound of the formula:

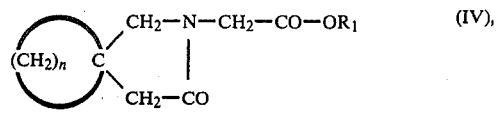

wherein n has the same meaning as above and $R_1$ is a straight or branched alkyl radical containing up to 4 carbon atoms, with an amine of the general formula:

wherein R has the same meaning as above.

The compounds of formula (IV) are new and valuable intermediates which also form part of the present invention. They can be prepared from the spirolactam compounds of formula (II) which, when n is 4 or 5, are known (see J. Ind. Chem. Soc., 5, 549 et seq./1928) and which can be prepared by cyclising compounds of the formula:

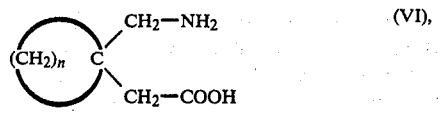

wherein n has the same meaning as above (these compounds VI are described in German Patent Specification No. 2,460,891) or their alkyl esters by splitting off water or alcohol. The free amino acids are heated in an appropriate organic solvent, for example acetic acid, acetic acid/benzene, benzene, toluene, dimethyl formamide or dimethyl sulphoxide.

The lactams (II) are also formed by heating the amino acid lower alkyl esters or salts in an appropriate solvent, for example methanol, ethanol, benzene, toluene, dimethyl formamide or a mixture thereof. Furthermore, lactamisation of the amino acids (VI) can be advantageously carried out in the presence of a water binding agent, for example acetic anhydride or acetyl chloride. In the last case, there are first obtained the N-acetyl-spirolactams which, by subsequent mild hydrolysis are converted into the spirolactams of formula (II). This, for example, is by treatment with an aqueous alcoholic alkali metal carbonate solution. The amino acid salts, such as the hydrochlorides or benzene-sulphonates, can also advantageously be used for the preparation of the lactams, sodium acetate preferably being added to the dehydration mixture for binding the acid.

The novel 3-oxo-2-azaspiro[4,6]-undecane (n=6) surprisingly possesses an anticonvulsive action and also forms part of the present invention.

The spirolactams of formula (II) are, by reaction with an alkali metal amide or hydride, such as sodamide or sodium hydride, potassium or lithium hydride, in an inert organic solvent, such as benzene, dioxan or toluene, first converted into the corresponding alkali metal salts which are then reacted, in the same solvent, with a haloacetic acid alkyl ester, preferably a chloroacetic acid alkyl ester (Variant b) or directly with a haloacetamide, preferably chloroacetamide (Variant a). In order to increase the speed of the reaction, it is preferred to carry out the N-substitution at an elevated temperature, preferably at the reflux temperature of the solvent employed. The preparation of the corresponding salts of the compounds (II) are prepared using organo-metal compounds, for example n-butyl lithium, in conventional methods.

From the N-spirolactam-acetic acid esters (IV) formed by the reaction of the spirolactam alkali metal salts (II) with haloacetic acid esters (III), there are obtained the compounds (I) according to the present invention in known manner by reaction with an amine of the general formula $H_2N.R$ (V), wherein R has the same meaning as above, in an appropriate solvent, for example methanol, ethanol, benzene, dioxan or dimethyl formamide or a mixture thereof, at a temperature of from 0° to 100° C. and preferably of from 25° to 70° C.

The following examples are given for the purpose of illustrating the present invention:

EXAMPLE 1

3-Oxo-2-azaspiro[4,5]decane-2-acetamide.

Variant (b)

4.3 g. Ethyl 3-oxo-2-azaspiro[4,5]decane-2-acetate (b.p. 130°–145° C./0.1 mm.Hg.) are taken up in 50 ml. saturated methanolic ammonia solution. The solution is left to stand overnight at ambient temperature and subsequently evaporated to dryness. After recrystallisation from methanol/diethyl ether/petroleum ether, there are obtained 3.4 g. (75% of theory) 3-oxo-2-azaspiro[4,5]-decane-2-acetamide; m.p. 144.5°–146° C.

Analysis: $C_{11}H_{18}N_2O_2$; calc.: C 62.86%; H 8.63%; N 13.31%; O 15.22%; found: 63.25%; 8.77%; 12.88%; 15.09%.

The ethyl 3-oxo-2-azaspiro[4,5]decane-2-acetate used as starting material is prepared as follows:

A solution of 3.25 g. 3-oxo-2-azaspiro[4.5]decane (see J. Ind. Chem. Soc., 5, 552/1928) in 20 ml. toluene is added dropwise, under an atmosphere of nitrogen, to a suspension of 0.53 g. sodium hydride in 20 ml. anhydrous toluene. After completion of the evolution of hydrogen, the reaction mixture is heated, while stirring, for 1 hour at 90° C. Thereafter, the reaction mixture is allowed to cool to about 60° C. and a solution of 2.62 g. ethyl 2-chloroacetate in 10 ml. anhydrous toluene is added thereto dropwise. Subsequently, the reaction mixture is heated to 100° C. for 2 hours. After cooling, the reaction mixture is partitioned between benzene and water and the organic phase is evaporated to dryness. By vacuum distillation of the residue, there are obtained 4.3 g. ethyl 3-oxo-2-azaspiro[4,5]decane-2-acetate; b.p. 130°–145° C./0.1 mm.Hg. (bulbed tube).

EXAMPLE 2

3-Oxo-2-azaspiro[4,4]nonane-2-acetamide.

Variant (b)

In a manner analogous to that described in Example 1, 7.5 g. ethyl 3-oxo-2-azaspiro[4,4]nonane-2-acetate are converted, by treatment with a saturated methanolic solution of ammonia, into 3-oxo-2-azaspiro[4,4]nonane-2-acetamide which, after recrystallisation from methanol/diethyl ether/n-hexane, is obtained in the form of a colourless substance; m.p. 118°–119° C.

Analysis: $C_{10}H_{16}N_2O_2$; calc.: C 61.20%; H 8.22%; N 14.27%; found: 61.23%; 8.22%; 13.72%.

The ethyl 3-oxo-2-azaspiro[4,4]nonane-2-acetate used as starting material is prepared in the following manner:

7.38 g. 3-oxo-2-azaspiro[4,4]nonane (see J. Ind. Chem. Soc., 5, 553/1928) are reacted with ethyl 2-chloroacetate in a manner analogous to that described in Example 1. After stripping off the solvent, there are obtained 7.5 g. ethyl 3-oxo-2-azaspiro[4,4]nonane-acetate; b.p. 125°–130° C./0.1 mm.Hg. This compound can be used directly.

EXAMPLE 3

3-Oxo-2-azaspiro[4,6]undecane-2-acetamide.

Variant (b)

9.7 g. ethyl 3-oxo-2-azaspiro[4,6]undecane-2-acetate are reacted with ammonia in a manner analogous to that described in Example 1. There are obtained 7.5 g. 3-oxo-2-azaspiro[4,6]undecane-2-acetamide which can be recrystallised from methanol/diethyl ether; m.p. 134°–135° C.

Analysis: $C_{12}H_{20}N_2O_2$; calc.: C 64.26%; H 8.99%; N 12.49%; O 14.26%; found: 64.70%; 8.74%; 12.52%; 14.05%.

The ethyl 3-oxo-2-azaspiro[4,6]undecane-2-acetate used as starting material can be prepared in the following manner:

13.7 g. 1,1-cycloheptane-diacetic anhydride are mixed with 2.36 g. anhydrous methanol in 10 ml. benzene and boiled under reflux for 2 hours. After evaporation in a vacuum, there are obtained 15.9 g. 1,1-cycloheptanediacetic acid monomethyl ester which is dissolved in 100 ml. anhydrous acetone and then, according to the description given in German Pat. No. 2,460,891, first mixed with 8.1 g. triethylamine in 30 ml. acetone, thereafter with 9.8 g. ethyl chloroformate in 30 ml. anhydrous acetone and finally with 6.5 g. sodium azide in 20 ml. water. After the reaction has taken place, the reaction mixture is extracted and the solution obtained of 1,1-cycloheptane-diacetic acid monomethyl ester azide in toluene is rearranged to give the isocyanate. The methyl 1-isocyanatomethyl-1-cycloheptane-acetate obtained is boiled under reflux for 3 hours in 20% hydrochloric acid. Upon concentration of the reaction mixture in a vacuum, 1-aminomethyl-1-cycloheptane-acetic acid separates out in the form of its hydrochloride. 32 g. 1-aminomethyl-1-cycloheptane-acetic acid hydrochloride, obtained from several reaction batches, and 45 g. anhydrous sodium acetate are heated under reflux for 5 hours in 300 ml. acetic anhydride. After cooling, inorganic salts are filtered off and the solvent is stripped off in a vacuum. Distillation of the residue gives N-acetyl-3-oxo-2-azaspiro[4,6]undecane in the form of a colourless oil; b.p. 125°–130° C./$10^{-3}$ mm.Hg.

38 g. N-acetyl-3-oxo-2-azaspiro[4,6]undecane are heated to 60° C. for 6 hours in a solution of 40 g. potassium carbonate in 400 ml. 80% aqueous ethanol. The reaction mixture is then acidified with dilute hydrochloric acid, the ethanol is stripped off in a vacuum and the aqueous residue is extracted with methylene chloride. The residue obtained after evaporation of the solvent gives, upon vacuum distillation, 3-oxo-2-azaspiro[4,6]undecane in the form of a colourless syrup; b.p. 125°–135° C./$10^{-3}$ mm.Hg. After crystallisation from diisopropyl ether, the compound melts at 70°–74° C.

Analysis: $C_{10}H_{17}NO$; calc.: C 71.81%; H 10.25%; N 8.38%; found: 71.99%; 10.27%; 8.25%.

9.1 g. of the 3-oxo-2-azaspiro[4,6]undecane thus obtained are reacted with 6.5 g. ethyl 2-chloroacetate in a manner analogous to that described in Example 1.

There is thus obtained ethyl 3-oxo-2-azaspiro[4,6]undecane-2-acetate (b.p. 135°–140° C./0.1 mm.Hg.), which can be directly subjected to ammonolysis.

EXAMPLE 4

3-Oxo-2-azaspiro[4,5]decane-2-(N-methyl)-acetamide.

Variant (a)

A slurry of 0.95 g. sodium hydride in 20 ml. anhydrous toluene is mixed with a solution of 5.5 g. 3-oxo-2-azaspiro-[4,5]decane in 20 ml. toluene. The reaction mixture is heated to 80° C. for 1 hour, while stirring. After allowing to cool, a solution of 4.33 g. N-methyl-chloroacetamide in 20 ml. toluene is slowly added thereto dropwise, whereafter the reaction mixture is heated under reflux for 3 hours. After working up the reaction mixture in the manner described in Example 1 and distillation of the crude product, there are obtained 4.5 g. 3-oxo-2-azaspiro[4,5]decane-2-(N-methyl)-acetamide in the form of a colourless syrup (b.p. 150°–160° C./$10^{-3}$ mm.Hg.) which can be crystallised from hexane; melting range 55°–65° C.

Analysis: $C_{12}H_{20}N_2O_2$; calc.: C 64.26%; H 8.99%; N 12.49%; found: 64.01%; 8.44%; 12.42%.

EXAMPLE 5

3-Oxo-2-azaspiro[4,4]nonane-2-(N-methyl)-acetamide.

Variant (a)

In a manner analogous to that described in Example 4, by the reaction of 3-oxo-2-azaspiro[4,4]nonane in the form of its sodium salt with N-methyl-bromoacetamide, there is obtained 3-oxo-2-azaspiro[4,4]nonane-2-(N-methyl)-acetamide, which can be recrystallised from chloroform/diethyl ether; m.p. 100°–102° C.

Analysis: $C_{11}H_{18}N_2O_2$; calc.: C 62.83%; H 8.63%; N 13.32%; found: 62.99%; 8.20%; 12.91%.

EXAMPLE 6

3-Oxo-2-azaspiro[4,6]undecane-2-(N-methyl)-acetamide.

Variant (a)

In a manner analogous to that described in Example 4, by the reaction of 3-oxo-2-azaspiro[4,6]undecane in the form of its sodium salt with N-methyl-chloroacetamide, there is obtained 3-oxo-2-azaspiro[4,6]undecane-2-(N-methyl)-acetamide (b.p. 160°–170° C./$10^{-3}$ mm.Hg.), which can be recrystallised from chloroform/diethyl ether/n-hexane; m.p. 78°–80° C.

EXAMPLE 7

3-Oxo-2-azaspiro[4,5]decane-2-(N-allyl)-acetamide.

Variant (a)

In a manner analogous to that described in Example 4, by the reaction of 3-oxo-2-azaspiro[4,5]decane in the form of its lithium salt with N-allyl-chloroacetamide, there is obtained 3-oxo-2-azaspiro[4,5]decane-2-(N-allyl)-acetamide which can be purified by chromatography on silica gel using benzene/chloroform (10–20%) as eluent, followed by vacuum distillation. 3-Oxo-2-azaspiro[4,5]decane-2-(N-allyl)-acetamide is obtained in the form of a colourless, viscous syrup; b.p. 160°–165° C./$10^{-2}$ mm.Hg.

Analysis: $C_{14}H_{22}N_2O_2$; calc.: C 67.17%; H 8.86%; N 11.19%; found: 67.29%; 8.88%; 10.95%.

EXAMPLE 8

3-Oxo-2-azaspiro[4,6]undecane-2-(N-allyl)-acetamide.

Variant (a)

In a manner analogous to that described in Example 4, by the reaction of 3-oxo-2-azaspiro[4,6]undecane in the form of its potassium salt with N-allyl-chloroacetamide, there is obtained 3-oxo-2-azaspiro[4,6]undecane-2-(N-allyl)-acetamide in the form of a colourless syrup; b.p. 150°–155° C./$10^{-3}$ mm.Hg.

Analysis: $C_{15}H_{24}N_2O_2$; calc.: C 68.15%; H 9.15%; N 10.60%; found: 67.80%; 9.03%; 10.94%.

EXAMPLE 9

3-Oxo-2-azaspiro[4,5]decane-(N-2-propynyl)-acetamide.

Variant (a)

In a manner analogous to that described in Example 4, by the reaction of 3-oxo-2-azaspiro[4,5]decane in the form of its sodium salt with N-2-propynyl-chloroacetamide, there is obtained 3-oxo-azaspiro[4,5]decane-2-(N-2-propynyl)-acetamide, which can be recrystallised from chloroform/diethyl ether/n-hexane; m.p. 101°–103° C.

Analysis: $C_{14}H_{20}N_2O_2$; calc.: C 67.72%; H 8.12%; N 11.28%; found: 67.93%; 8.37%; 11.53%.

EXAMPLE 10

3-Oxo-2-azaspiro[4,6]undecane-2-(N-2-propynyl)-acetamide.

Variant (a)

In a manner analogous to that described in Example 4, by the reaction of 3-oxo-2-azaspiro[4,6]undecane in the form of its sodium salt with N-2-propynyl-chloroacetamide, there is obtained 3-oxo-2-azaspiro[4,-6]undecane-2-(N-2-propynyl)-acetamide (b.p. 170°–175° C./$10^{-3}$ mm.Hg.), which can be recrystallised from chloroform/diethyl ether/n-hexane.

Analysis: $C_{15}H_{22}N_2O_2$; calc.: C 68.67%; H 8.45%; N 10.68%; found: 68.54%; 8.11%; 10.23%.

The following compounds can also be prepared in a manner analogous to that described in the preceding Examples:

3-oxo-2-azaspiro[4,5]decane-2-(N-n-pentyl)-acetamide
3-oxo-2-azaspiro[4,5]decane-2-(N-isopropyl)-acetamide
3-oxo-2-azaspiro[4,5]decane-2-(N-ethyl)-acetamide
3-oxo-2-azaspiro[4,5]decane-2-(N-2-methylallyl)-acetamide
3-oxo-2-azaspiro[4,6]undecane-2-(N-2-methylallyl)-acetamide
3-oxo-2-azaspiro[4,6]undecane-2-(N-ethyl)-acetamide
3-oxo-2-azaspiro[4,6]undecane-2-(N-butyl)-acetamide.

The effectiveness of the new compounds of formula (I) invention was demonstrated by comparative experiments. All the experiments were carried out on male mice with a body weight of 18 to 25 g. The animals fasted for 24 hours prior to the experiment, but water was available ad libitum.

Water-soluble compounds were administered intragastrally in aqueous solution. Water-insoluble compounds were suspended in a 1% tragacanth mucilage and administered intragastrally by means of a metal probe.

The semicarbazide cramp was induced by the subcutaneous administration of 1000 mg/kg. of semicarbazide hydrochloride and the animals observed for 110 minutes after administration of the test compound.

In the case of the pentetrazole cramp 120 mg./kg. pentetrazole was administered subcutaneously and the animals observed for 50 minutes after administration of the test compound.

The protective action in the cramp models was determined in comparison with a control group in which all animals manifested cramp phenomena.

In the following Table, there is given the number of animals in %, referred to the control group, which, after administration of the test substance, showed no symptoms of cramp and thus proved to be protected.

The following compounds were used as comparison substances:
A = β-p-chlorophenyl-γ-aminobutyric acid
B = sodium n-propyl-valerate Since it is known that piracetam shows no action in the cramp models used, this structurally similar compound could not be used for comparison purposes. The same applies to γ-aminobutyric acid since it is known that this compound cannot pass the blood-brain barrier.

The following representative compounds were investigated:
1 = 3-oxo-2-azaspiro[4,5]decane-2-acetamide (Example 1)
2 = 3-oxo-2-azaspiro[4,5]undecane-2-(N-allyl)-acetamide (Example 7)
3 = 3-oxo-2-azaspiro[4,6]undecane-2-(N-methyl)-acetamide (Example 6)
4 = 3-oxo-2-azaspiro[4,6]undecane-2-(N-propynyl)-acetamide.

The dosage above which side-effects could be ascertained is underlined in the following Table.

TABLE

| Compound No. | dose in mg/kg | anticonvulsive action as percentage of the protected animals at the given dosage | | toxicity mg/kg |
|---|---|---|---|---|
| | | semicarbazide cramp | pentetrazole cramp | |
| 1 | 62.5 ig | 34 | | from 400 ig slight side effects |
| | 125.0 ig | 63 | | |
| | 250.0 ig | 65 | no action | |
| | 360.0 ig | 88 | | |
| | 432.0 ig | 88 | | |
| 2 | 100.0 ig | 56 | | from 200 ig slight ataxia |
| | 125.0 ig | 40 | 30 | |
| | 250.0 ig | 100 | | |
| 3 | 100.0 ig | 57 | | from 200 ig slight ataxia |
| | 125.0 ig | | 30 | |
| | 250.0 ig | 80 | | |
| 4 | 250.0 ig | 89 | 50 | at 200 ig commencement of ataxia and sedation |
| comparison A | 3.125 ig | 43 | | at 3.125 ig from 12.5 ig severe side effects |
| | 6.25 ig | 86 | | |
| | 12.5 ig | 100 | | |
| | 25.0 ig | 100 | 0 | |
| | 50.0 ig | | 20 | |
| | 100.0 ig | | 50 | |
| comparison B | 50.0 ig | 0 | | from 50 ig side effects |
| | 100.0 ig | 50 | | |
| | 200.0 ig | 88 | | |
| | | 100 | | |
| | 250.0 ig | | 60 | |

The new compounds according to the present invention differ from the comparative compounds by having a substantially more favorable toxicity behavior, as can be seen from Table I. In particular, they are characterized in that the anti-convulsive action is manifested at a dosage having no side effects. Furthermore, the side effects observed at higher dosage levels are, with the same strength of action, of a milder nature.

A further advantage of compounds according to the present invention is the simultaneous effectiveness in the pentetrazole and semicarbazide cramp model in the sub-toxic dosage range; they are characterized by a greater spectrum of activity. In this way, the compounds provide the possibility to treat epilepsy, for example, of varying causes with the same active material.

Because of their low toxicity, the compounds can be administered enterally or parenterally within wide dosages, in admixture with conventional liquid or solid pharmaceutical diluents or carriers having the conventional additives, for example, tartrate and citrate buffers, ethanol and complex-forming agents (such as ethylenediamine-tetraacetic acid and the non-toxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol); compositions suitable for oral administration can, if desired, also contain flavoring and/or sweetening agents.

The individual dosage of the compounds according to the present invention is 5–50 mg. parenterally and 20–200 mg. enterally.

We claim:

1. A compound of the formula:

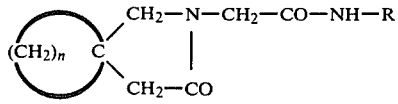

wherein R is hydrogen, alkyl of from 1 to 5 carbon atoms, or unsaturated alkyl of from 2 to 5 carbon atoms and n is 4, 5, or 6.

2. A compound according to claim 1 wherein R contains 1 to 3 carbon atoms.

3. A compound according to claim 2 wherein R is selected from the group consisting of methyl, ethyl, n-propyl, isopropyl, allyl and propynyl.

4. A compound according to claim 1 wherein n is 4.

5. The compound of claim 4 which is 3-Oxo-2-azaspiro[4,4]nonane-acetamide.

6. The compound of claim 4 which is 3-Oxo-2-azaspiro[4,4]nonane-2-(N-methyl)-acetamide.

7. A compound according to claim 1 wherein n is 5.

8. The compound of claim 7 which is 3-Oxo-2-azaspiro[4,5]decane-2-acetamide.

9. The compound of claim 7 which is 3-Oxo-2-azaspiro[4,5]decane-2-(N-methyl)-acetamide.

10. The compound of claim 7 which is 3-Oxo-2-azaspiro[4,5]decane-2-(N-allyl)-acetamide.

11. The compound of claim 7 which is 3-Oxo-2-azaspiro[4,5]decane-(N-2-propynyl)-acetamide.

12. The compound of claim 7 which is 3-Oxo-2-azaspiro[4,5]decane-2-(N-n-pentyl)-acetamide.

13. The compound of claim 7 which is 3-Oxo-2-azaspiro[4,5]decane-2-(N-isopropyl)-acetamide.

14. The compound of claim 7 which is 3-Oxo-2-azaspiro[4,5]decane-2-(N-ethyl)-acetamide.

15. The compound of claim 7 which is 3-Oxo-2-azaspiro[4,5]decane-2-(N-2-methylallyl)-acetamide.

16. A compound according to claim 1 wherein n is 6.

17. The compound of claim 16 which is 3-Oxo-2-azaspiro[4,6]undecane-2-acetamide.

18. The compound of claim 16 which is 3-Oxo-2-azaspiro[4,6]undecane-2-(N-methyl)-acetamide.

19. The compound of claim 16 which is 3-Oxo-2-azaspiro[4,6]undecane-2-(N-allyl)-acetamide.

20. The compound of claim 16 which is 3-Oxo-2-azaspiro[4,6]undecane-2-(N-2-propynyl)-acetamide.

21. The compound of claim 16 which is 3-Oxo-2-azaspiro[4,6]undecane-2-(N-2-methylallyl)-acetamide.

22. The compound of claim 16 which is 3-Oxo-2-azaspiro[4,6]undecane-2-(N-ethyl)-acetamide.

23. The compound of claim 16 which is 3-Oxo-2-azaspiro[4,6]undecane-2-(N-butyl)-acetamide.

24. A pharmaceutical composition useful for the treatment of convulsions which comprises an anti-convulsive effective amount of at least one compound of the formula:

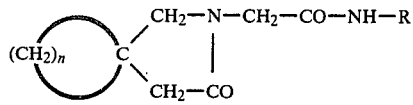

wherein R is hydrogen, alkyl of from 1 to 5 carbon atoms or unsaturated alkyl of from 2 to 5 carbon atoms and n is 4, 5 or 6 in admixture with a solid or liquid pharmaceutical diluent or carrier.

* * * * *